(12) United States Patent
Taepke, II et al.

(10) Patent No.: US 10,173,069 B2
(45) Date of Patent: Jan. 8, 2019

(54) MEDICAL DEVICE FIXATION

(75) Inventors: Robert T. Taepke, II, Coon Rapids, MN (US); Ya Guo, Santa Rosa, CA (US); Joseph D. Berglund, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 851 days.

(21) Appl. No.: 13/586,572

(22) Filed: Aug. 15, 2012

(65) Prior Publication Data

US 2013/0192611 A1 Aug. 1, 2013

Related U.S. Application Data

(60) Provisional application No. 61/591,051, filed on Jan. 26, 2012.

(51) Int. Cl.
| | |
|---|---|
| A61B 5/02 | (2006.01) |
| A61F 2/06 | (2013.01) |
| A61F 2/07 | (2013.01) |
| A61F 2/852 | (2013.01) |
| A61N 1/375 | (2006.01) |
| A61B 5/0215 | (2006.01) |
| A61B 5/021 | (2006.01) |
| A61F 13/00 | (2006.01) |
| A61B 5/0265 | (2006.01) |
| A61B 5/026 | (2006.01) |

(52) U.S. Cl.
CPC ............ *A61N 1/375* (2013.01); *A61B 5/02* (2013.01); *A61B 5/021* (2013.01); *A61B 5/026* (2013.01); *A61B 5/0215* (2013.01); *A61B 5/0265* (2013.01); *A61B 5/02152* (2013.01); *A61F 2/06* (2013.01); *A61F 2/07* (2013.01); *A61F 2/852* (2013.01); *A61F 2013/0094* (2013.01); *A61F 2250/003* (2013.01); *A61F 2250/0031* (2013.01)

(58) Field of Classification Search
CPC .................................................. A61F 2250/0031
USPC ........................................................ 623/1.36
See application file for complete search history.

(56) References Cited

U.S. PATENT DOCUMENTS

| | | |
|---|---|---|
| 4,281,669 A | 8/1981 | MacGregor |
| 4,628,944 A | 12/1986 | MacGregor et al. |
| 4,997,440 A | 3/1991 | Dumican |
| 6,162,537 A | 12/2000 | Martin et al. |

(Continued)

FOREIGN PATENT DOCUMENTS

EP 0923912 A2 * 6/1999 ............... A61F 2/06

OTHER PUBLICATIONS

"A Bioabsorbable Metal Stent: What DREAMS Are Made of," Qmed, found at http://www.qmed.com/mpmn/medtechpulse/bioabsorbable-metal-stent-what-dreams-are-made?cid=nl_mpmn_medtech_pulse, posted Sep. 5, 2012, 1 p.

(Continued)

*Primary Examiner* — Jacqueline Woznicki

(57) ABSTRACT

A fixation device configured to anchor an implantable medical device within a patient includes a temporary biodegradable fixation mechanism configured to secure the device after implantation until the temporary fixation mechanism biodegrades and a chronic fixation mechanism configured to promote tissue growth that secures the device to tissue of the patient before the temporary fixation mechanism biodegrades.

35 Claims, 10 Drawing Sheets

(56) References Cited

U.S. PATENT DOCUMENTS

| | | | | |
|---|---|---|---|---|
| 6,277,078 | B1* | 8/2001 | Porat | A61B 5/0031 600/486 |
| 7,499,757 | B2 | 3/2009 | Coe et al. | |
| 7,509,169 | B2 | 3/2009 | Eigler et al. | |
| 7,617,007 | B2 | 11/2009 | Williams et al. | |
| 7,797,053 | B2 | 9/2010 | Atkinson et al. | |
| 7,953,498 | B1* | 5/2011 | Carbunaru et al. | 607/118 |
| 8,303,511 | B2* | 11/2012 | Eigler | A61B 5/0215 600/481 |
| 2003/0036803 | A1 | 2/2003 | Mcghan | |
| 2005/0288596 | A1* | 12/2005 | Eigler | A61B 5/0215 600/485 |
| 2006/0025785 | A1 | 2/2006 | Cully et al. | |
| 2006/0079740 | A1* | 4/2006 | Silver et al. | 600/309 |
| 2007/0190037 | A1* | 8/2007 | Flugelman | A61K 31/70 424/93.7 |
| 2008/0119877 | A1 | 5/2008 | Deusch et al. | |
| 2009/0088813 | A1 | 4/2009 | Brockway et al. | |
| 2009/0105822 | A1 | 4/2009 | Ogilvie | |
| 2009/0171448 | A1* | 7/2009 | Eli | A61B 17/22 623/1.32 |
| 2010/0070019 | A1* | 3/2010 | Shalev | 623/1.15 |
| 2011/0251516 | A1* | 10/2011 | Doerr | A61B 5/07 600/562 |
| 2011/0264186 | A1* | 10/2011 | Berglung et al. | 623/1.11 |

OTHER PUBLICATIONS

O'Brien et al., "The evolution of cardiovascular stent materials and surfaces in response to clinical drivers: A review," Acta Biomaterilia 5 (2009):945-58.

Ormiston et al., "Bioabsorbable Coronary Stents," Circ Cardiovasc Intervent. Jun. 2009;2(3):255-60.

Witte, "The history of biodegradeable magnesium implants: a review" Acta Biomaterialia 6 (2010):1680-1692.

Witte et al., "Biodegradeable magnesium scaffolds: Part 1: Appropriate inflammatory response," Journal of Biomedical Materials Research Part A, 81(3):748-56, 2007.

"Bioabsorbable Stents Could Make Big Bucks for Abbott, Other Innovators," http://www.qmed.com/mpmn/blog/26891/bioabsorbable-stents-could-make-big-bucks-abbott-other-innovators, retrieved Dec. 9, 2010, 1 p.

"Bioabsorbable Stent Sparks New Design Debate," http://www.qmed.com/mpmn/blog/24080/bioabsorbable-stent-sparks-new-design-debate, retrieved Dec. 9, 2010, 1 p.

"Cardiologists Preference for Bioabsorbable Stents will Boost Interventional Cardiology Market," Medical Device Summit, Nov. 29, 2010, 2 pp.

O'Riordan, "Now you see me, now you don't: The bioabsorbable stent in clinical practice," Nov. 8, 2010, http://www.theheart.org/article/1144463.do, 6 pp.

Anneaux et al., "The Promise of Biodegradable Polymers," Medical Device Summit, http://www.medicaldevicesummit.com/ProductDevelopment/News/The-Promise-of-Biodegradable-Polymers-98.aspx, Mar. 22, 2010, 4 pp.

Waksman, "Biodegradable Stents: They Do Their Job and Disappear," Journal of Invasive Cardiology, vol. 18, No. 2, pp. 70-74, Feb. 2006.

U.S. Appl. No. 13/050,417, by Kamal Deep Mothilal, filed Mar. 17, 2011.

Garg et al., "Biodegradable stents and non-biodegradable stents," Minerva Cardioangiologica Oct. 2009; 57(5):537-565.

Waksman, "Update on Bioabsorbable Stents: From Bench to Clinical," Journal of Interventional Cardiology, vol. 19, No. 5, pp. 414-421, Oct. 2006.

Waksman, "Promise and challenges of bioabsorbable stents," Catheterization and Cardiovascular Interventions, vol. 70, issue 3, pp. 407-414, Sep. 2007.

Ramcharitar et al., "Fully Biodegradable Coronary Stents: Progress to Date," American Journal of Cardiovascular Drugs, vol. 8, No. 5, pp. 305-314, Sep. 2008.

* cited by examiner

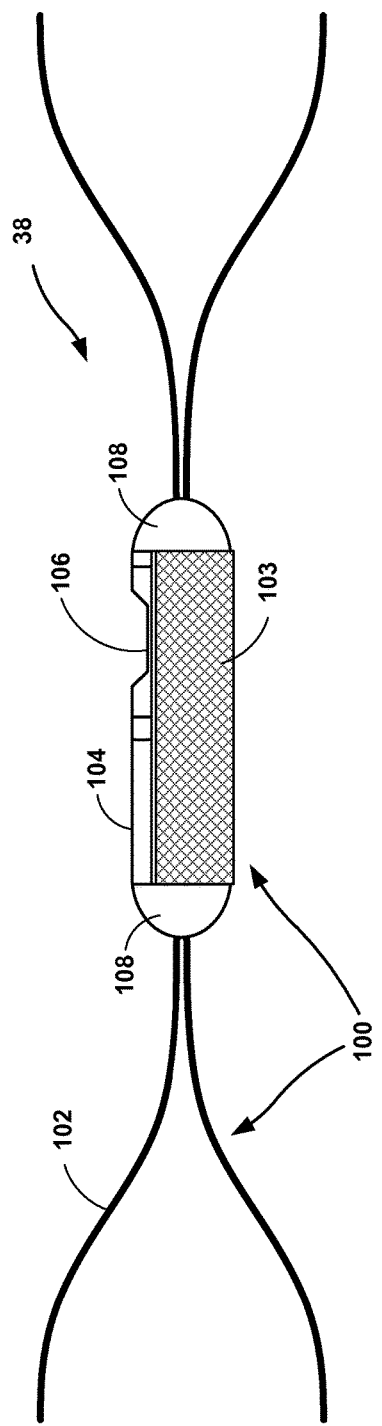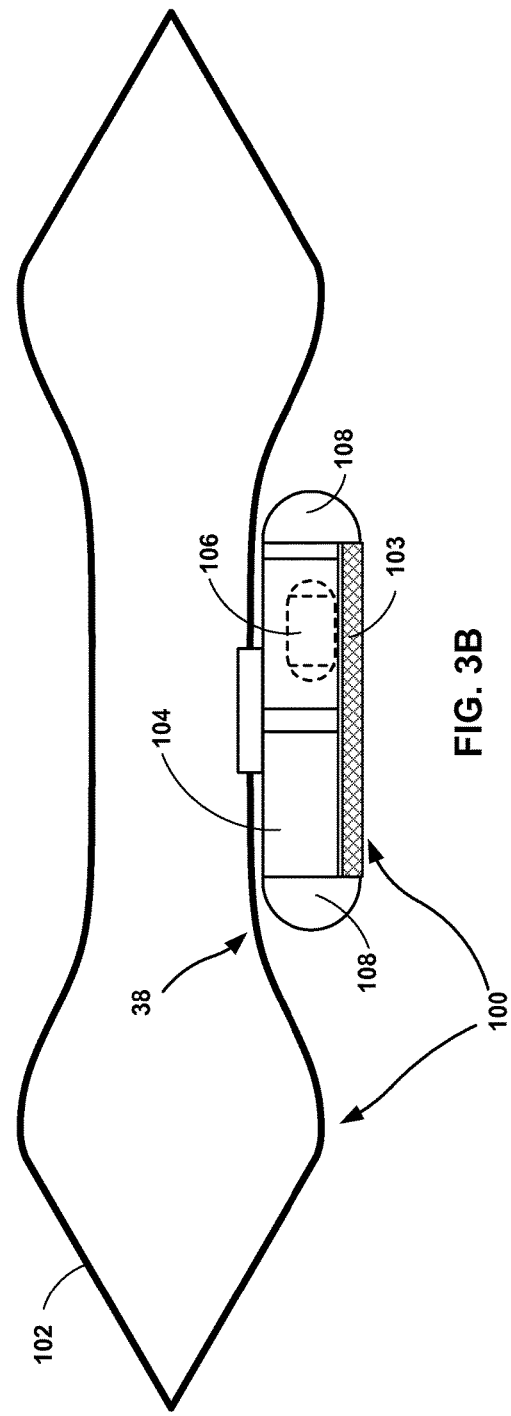
FIG. 3A
FIG. 3B

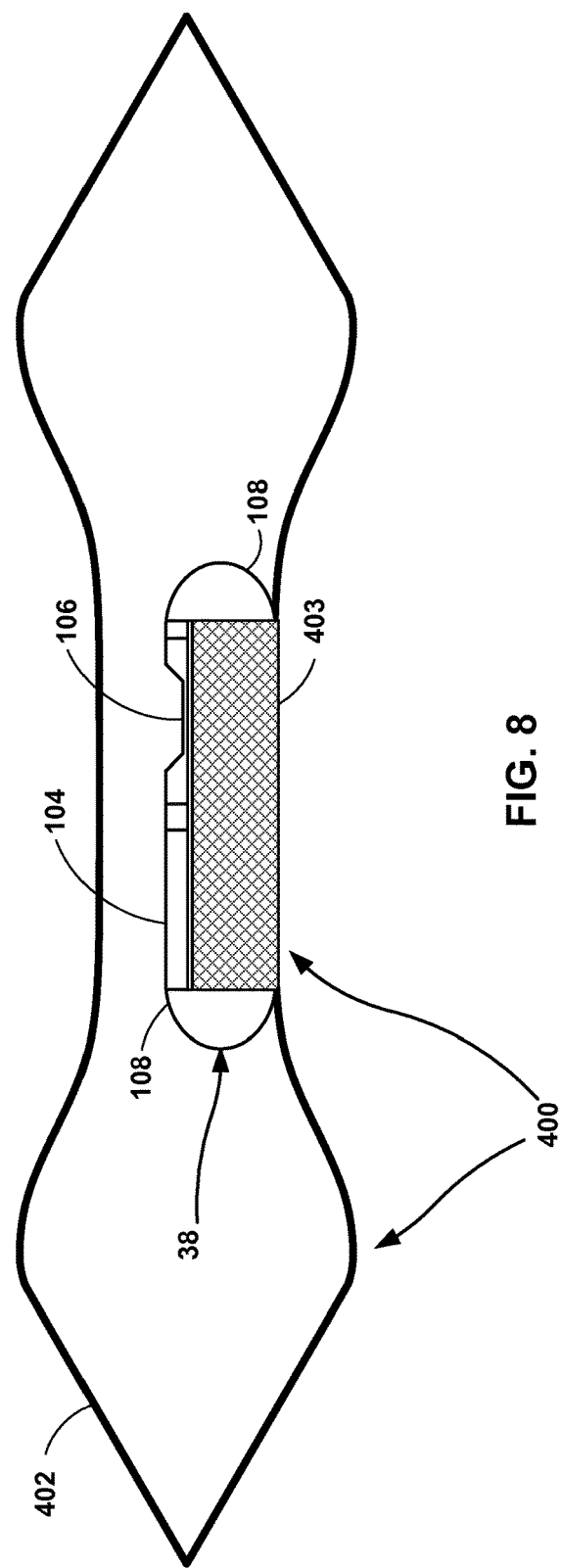

MEDICAL DEVICE FIXATION

This application claims the benefit of U.S. Provisional Patent Application No. 61/591,051, filed Jan. 26, 2012, the entire content of which is incorporated herein by reference.

TECHNICAL FIELD

The disclosure relates to medical devices and, more particularly, fixation of medical devices.

BACKGROUND

A variety of implantable medical devices for delivering a therapy and/or monitoring a physiological condition have been clinically implanted or proposed for clinical implantation in patients. Implantable medical devices may deliver electrical stimulation or pharmacologic therapy to, and/or monitor conditions associated with, the heart, muscle, nerve, brain, stomach or other organs or tissue, as examples. Some implantable medical devices may employ one or more elongated electrical leads carrying stimulation electrodes, sense electrodes, and/or other sensors. Implantable medical leads may be configured to allow electrodes or other sensors to be positioned at desired locations—either physically, or virtually (enabled/disabled electronically)—for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry. Other implantable medical devices may be leadless and include, for example, one or more electrodes (e.g., sense and/or stimulation electrodes) on an outer surface of the medical device.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

SUMMARY

In general, this disclosure is directed to fixation devices for implantable medical devices, which include a temporary biodegradable fixation mechanism configured to secure the device after implantation until the temporary fixation mechanism degrades and a chronic fixation mechanism configured to promote tissue growth that secures the device to the tissue of the patient after the temporary fixation mechanism biodegrades. Advantages of examples according to this disclosure may include reducing the size or "footprint" of a permanent fixation system, thereby suiting the structure better to the surrounding anatomy of an implant site, promoting a less invasive chronic milieu, higher safety, and greater reliability.

In one example, a fixation device for an implantable medical device (IMD). The fixation device includes a temporary fixation mechanism and a chronic fixation mechanism, both of which are configured to be connected to the IMD. The chronic fixation mechanism is configured to be connected to a first side of the IMD. The temporary fixation mechanism includes a biodegradable material and is configured to anchor the IMD within a blood vessel of a patient after implantation until the temporary fixation mechanism biodegrades. The chronic fixation mechanism is configured to promote tissue growth that anchors the IMD within the blood vessel before the temporary fixation mechanism biodegrades. The temporary fixation mechanism is configured to anchor the IMD within the blood vessel such that the first side of the IMD including the chronic fixation mechanism is arranged against endothelium of the blood vessel.

In another example, an implantable medical device (IMD) includes a body and a fixation device connected to the body of the IMD. The fixation device includes a temporary fixation mechanism and a chronic fixation mechanism. The temporary fixation mechanism includes a biodegradable material and is configured to anchor the IMD within a blood vessel of a patient after implantation until the temporary fixation mechanism biodegrades. The chronic fixation mechanism is connected to a first side of the body and configured to promote tissue growth that anchors the IMD within the blood vessel of the patient before the temporary fixation mechanism biodegrades. The temporary fixation mechanism is configured to anchor the IMD within the blood vessel such that the first side of the body including the chronic fixation mechanism is arranged against endothelium of the blood vessel.

Another example includes a method of securing an implantable medical device (IMD) within the body of a patient. The method includes arranging the IMD at a target location within a blood vessel of the patient, temporarily anchoring the IMD within the blood vessel with a temporary fixation mechanism including a biodegradable material and configured to secure the IMD within the blood vessel after implantation until the temporary fixation mechanism biodegrades, and chronically anchoring the IMD within the blood vessel with a chronic fixation mechanism connected to a first side of the IMD and configured to promote tissue growth that secures the IMD within the blood vessel before the temporary fixation mechanism biodegrades. The temporary fixation mechanism is configured to anchor the IMD within the blood vessel such that the first side of the IMD including the chronic fixation mechanism is arranged against endothelium of the blood vessel.

The details of one or more examples disclosed herein are set forth in the accompanying drawings and the description below. Other features, objects, and advantages will be apparent from the description and drawings, and from the claims.

BRIEF DESCRIPTION OF DRAWINGS

FIGS. 3A and 3B are elevation and plan views, respectively, of an implantable sensor including an example fixation device according to this disclosure.

FIG. 8 is a plan view of an implantable sensor including another example fixation device according to this disclosure.

DETAILED DESCRIPTION

Figure 1:
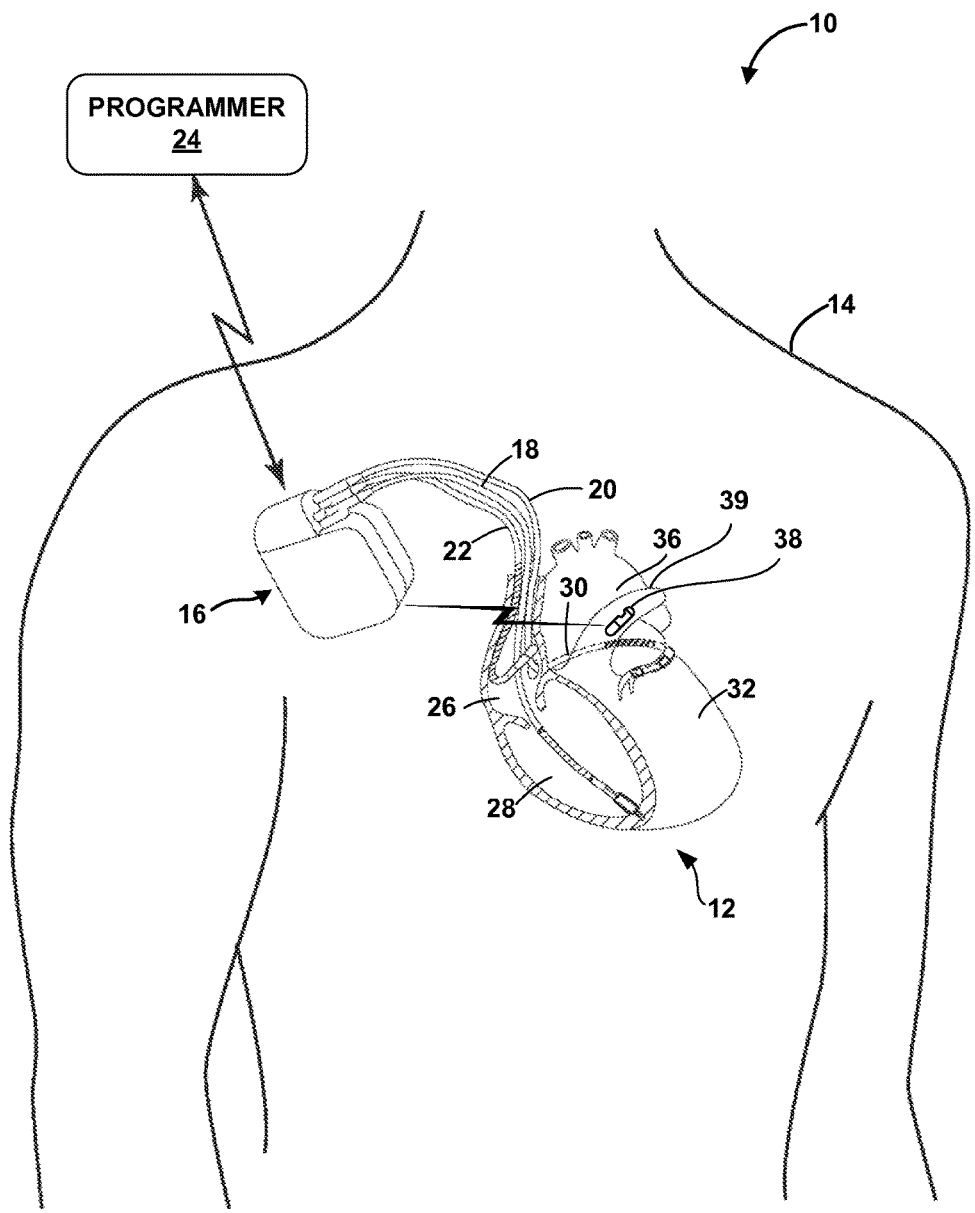
FIG. 1 is a conceptual drawing illustrating an example system that includes an implantable medical device (IMD) coupled to implantable medical leads and a leadless sensor.

The following examples are directed to techniques for securing medical devices within the body of a patient. Implantable medical devices (IMD) may be subject to various forces within the body of a patient, which may act to cause such devices to migrate from a particular implantation location and/or target tissue site for the implantable medical device. Fixation devices, including, e.g., barbs, tines, stents and other such structures, may be employed to help secure (or fix or anchor) medical devices within a patient and to help prevent or inhibit migration of the device. Forces within the body of a patient acting on an IMD and/or other devices attached to the IMD may also cause the IMD and/or attached devices to erode through tissue, which is undesirable, and may risk the integrity of fixation and/or of the implant site itself.

Increasing effort is being expended to design and market miniaturized medical devices. These include "leadless" pacemakers, "leadless" sensors, subcutaneously injectable monitoring devices (e.g. Medtronic's "Injectible Reveal"), and perhaps in the future, intravascularly injectable "micro-labs" or "nano-labs" that periodically, or even continually perform blood assays and report results back to an extra-corporeal monitoring device that gathers the data, aggregates it, and reports it to a medical professional. These implantable "micro-labs" or "nano-labs" may also communicate with other devices chronically implanted in the body. One purpose of this may be for the micro-lab or nano-lab to communicate information to a chronically implanted device. Another purpose may be in order to take advantage of the ability of a larger implanted device to serve as a "repeater", i.e. to re-transmit the signal over longer distances to an external monitoring system.

One of the challenges in implanting miniature devices within the cardiovascular system, including implanting leadless pacemakers and sensors, is fixation. Devices typically have an apparatus that holds them in place. For example, some pacing leads have tines or a helix at the tip to provide fixation. Inferior vena cava filters and other devices held within blood vessels employ a variety of stents to hold them in the vessel. One common feature of all the foregoing techniques is that the fixation device remains in the body permanently. The character and chronic placement of such fixation devices may produce a number of risks for a patient within whom the devices are implanted. For example, vascular stents, such as Nitinol stents or frames are known to fracture, posing a potential safety hazard. Second, stents and other fixation devices, such as tines or barbs, placed in certain vessels can erode through vessel walls. Third, stents are potentially thrombogenic. While stents can be coated with agents to reduce thrombosis, even coated stents may require anti-thrombotic therapy for some period of time, e.g., 12-months after implantation. Finally, metallic stents and other fixation devices, such as tines or barbs, may be unsafe for certain procedures, including, e.g., Magnetic Resonance Imagining (MRI).

In view of the foregoing challenges with current fixation devices that may be employed to secure miniature medical devices, examples according to this disclosure include a temporary fixation mechanism and a chronic fixation mechanism configured to be connected to an IMD. The temporary fixation mechanism includes a biodegradable material and is configured to anchor the IMD to tissue of a patient after implantation until the temporary fixation mechanism degrades. The chronic fixation mechanism is configured to promote tissue growth that secures the device to the tissue of the patient before the temporary fixation mechanism degrades. Example fixation devices according to this disclosure may be employed virtually anywhere in the vascular system, including within the chambers of the heart, but may prove especially useful in larger vessels, to eliminate the need for large stents or other large fixation mechanisms that could produce adverse effects over time. Additionally, examples according to this disclosure may be especially useful in the case of implanted devices, e.g. micro- or nano-sensing systems that are small compared to the fixation mechanism normally required to chronically anchor such devices within a vessel or cavity.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

IMD 16 may include electronics and other internal components necessary or desirable for executing the functions associated with the device. In one example, IMD 16 includes one or more processors, memory, a signal generator, sensing module and telemetry modules, and a power source. In general, memory of IMD 16 may include computer-readable instructions that, when executed by a processor of the IMD, cause it to perform various functions attributed to the device herein. For example, a processor of IMD 16 may control the signal generator and sensing module according to instructions and/or data stored on memory to deliver therapy to patient 14 and perform other functions related to treating condition(s) of the patient with IMD 16.

The signal generator of IMD 16 may generate electrical stimulation that is delivered to patient 12 via electrode(s) on one or more of leads 18, 20, and 22, in order to provide, e.g., cardiac sensing, pacing signals, or cardioversion/defibrillation shocks. The sensing module of IMD 16 may monitor electrical signals from electrode(s) on leads 18, 20, and 22 of IMD 16 in order to monitor electrical activity of heart 12. In one example, the sensing module may include a switch module to select which of the available electrodes on leads 18, 20, and 22 of IMD 16 are used to sense the heart activity. Additionally, the sensing module of IMD 16 may include multiple detection channels, each of which includes an amplifier, as well as an analog-to-digital converter for digitizing the signal received from a sensing channel for, e.g., electrogram signal processing by a processor of the IMD.

A telemetry module of IMD 16 may include any suitable hardware, firmware, software or any combination thereof for communicating with another device, such as programmer 24 (FIG. 1). Under the control of a processor of IMD 16, the telemetry module may receive downlink telemetry from and send uplink telemetry to programmer 24 with the aid of an antenna, which may be internal and/or external.

The various components of IMD 16 may be coupled to a power source, which may include a rechargeable or non-rechargeable battery. A non-rechargeable battery may be capable of holding a charge for several years, while a rechargeable battery may be inductively charged from an external device, e.g., on a daily or weekly basis.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

System 10 also includes vascular sensor 38. Sensor 38 is implanted in pulmonary artery 39. In one example, sensor 38 is configured to sense blood pressure of patient 14. For example, sensor 28 may be arranged in pulmonary artery 39 and be configured to sense the pressure of blood flowing from the right ventricle outflow tract (RVOT) from right ventricle 28 through the pulmonary valve to pulmonary artery 39. Sensor 38 may therefore directly measure pulmonary artery diastolic pressure (PADP) of patient 14. The PADP value is a pressure value that can be employed in patient monitoring. For example, PADP may be used as a basis for evaluating congestive heart failure in a patient. In other examples, however, sensor 38 may be employed to measure blood pressure values other than PADP. For example, sensor 38 may be arranged in right ventricle 28 of heart 14 to sense RV systolic or diastolic pressure. Moreover, the placement of sensor 38 is not restricted necessarily to the pulmonary side of the circulation. In one example, sensor 38 may be arranged in the systemic side of the circulation—e.g. in the left atrium, left ventricle, or aorta. Additionally, sensor 38 may be arranged outside of the cardiovascular system, including, e.g., arranging sensor 38 in a renal vessel. In such examples, sensor 38 may still be configured to communicate with IMD 16 and/or with one or more electrodes or other sensors on leads 18, 20, or 22. Arranging sensor 38 in the renal system may be appropriate, e.g., in a case in which IMD 16 is configured to treat heart failure by including some estimate of the degree of renal insufficiency in a patient. In one example according to this disclosure, a temporary fixation mechanism may be used to hold sensor 38 to the epicardium of heart 12 of patient 14, while a chronic fixation mechanism promotes tissue growth to chronically anchor sensor 38 in that location.

In some examples, sensor 38 includes a pressure sensor configured to respond to the absolute pressure inside pulmonary artery 39 of patient 14. Sensor 38 may be, in such examples, any of a number of different types of pressure sensors. One form of pressure sensor that may be useful for measuring blood pressure inside a human heart is a capacitive pressure sensor. Another example pressure sensor is an inductive sensor. In some examples, sensor 38 may also be a piezoelectric or piezoresistive pressure transducer. In other examples, sensor 38 may include a fluid flow, optical, glucose, or a heart sound sensor.

Figure 2:
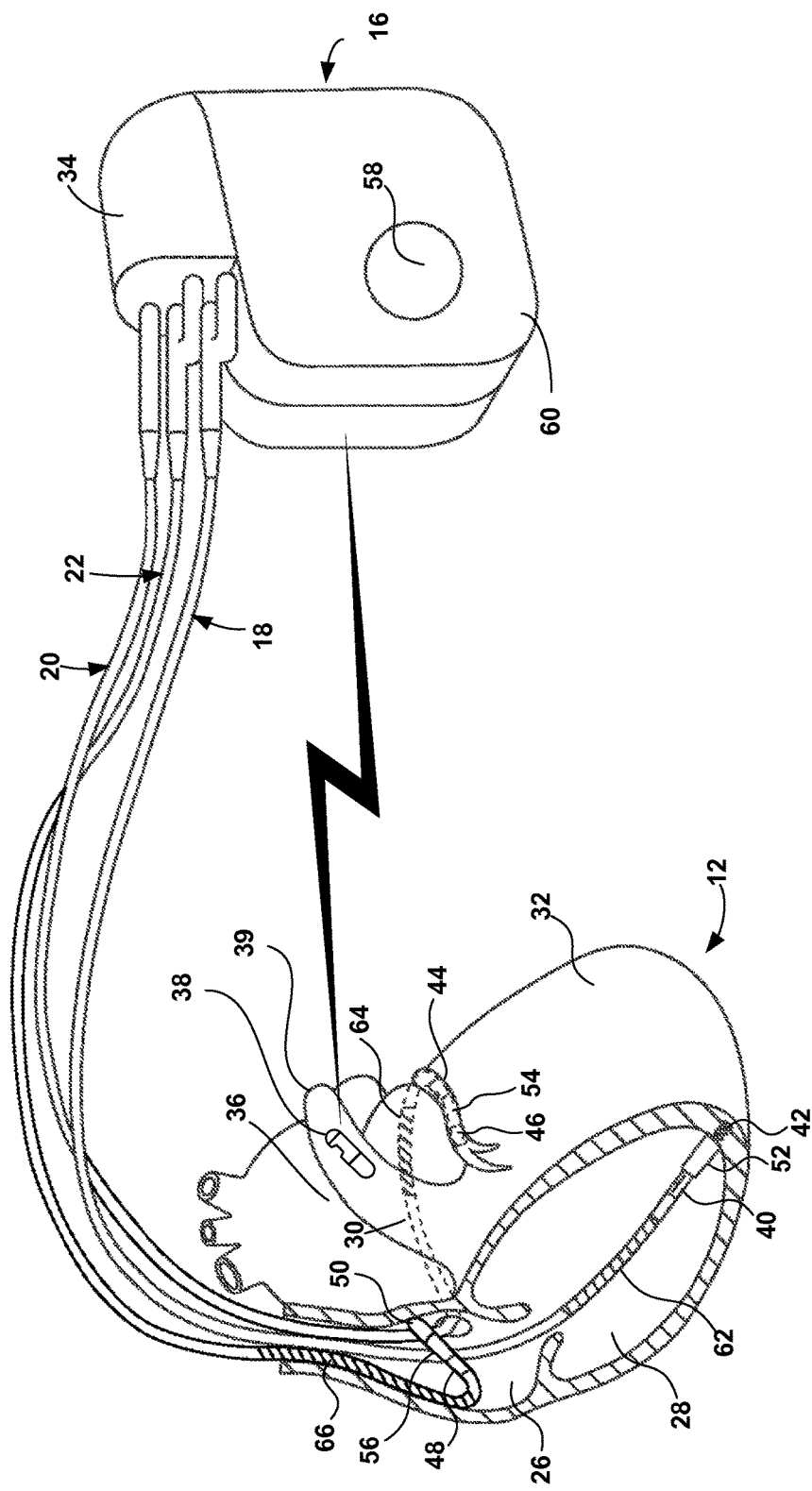
FIG. 2 is a conceptual drawing illustrating in greater detail the example IMD, leads, and sensor of FIG. 1 in conjunction with a heart.

In one example, sensor 38 is a leadless pressure sensor including capacitive pressure sensing elements configured to measure blood pressure within pulmonary artery 39. As illustrated in FIGS. 1 and 2, sensor 38 may be in wireless communication with IMD 16, e.g., in order to transmit blood pressure measurements to the IMD. Sensor 38 may employ, e.g., radio frequency (RF) or other telemetry techniques for communicating with IMD 16 and other devices, including, e.g., programmer 24. In another example, sensor 38 may include a tissue conductance communication (TCC) system by which the device employs tissue of patient 14 as an electrically conductive communication medium over which to send and receive information to and from IMD 16 and other devices.

As described in greater detail below, sensor 38 may include a fixation device according to this disclosure including a temporary biodegradable fixation mechanism and a tissue-growth promoting chronic fixation mechanism configured to secure the sensor within pulmonary artery 39 or to another target tissue site if sensor 38 is implanted at another location within patient 14. In one example, the fixation device securing sensor 38 includes a temporary fixation mechanism and a chronic fixation connected to sensor 38. The temporary fixation mechanism includes a biodegradable material and is configured to anchor sensor 38 within pulmonary artery 39 until the temporary fixation mechanism degrades. The chronic fixation mechanism is configured to promote tissue growth that secures sensor 38 within pulmonary artery 39, e.g. within the lumen of the artery and against the endothelium, before the temporary fixation mechanism degrades. For example, once the chronic fixation mechanism has completely anchored sensor 38 to the endothelium within the lumen of pulmonary artery 39, the temporary fixation mechanism may be designed to begin biodegrading in a substantially uniform, safe manner, leaving sensor 38 anchored in pulmonary artery 39 by tissue ingrowth facilitated by the chronic fixation mechanism. Example fixation devices according to this disclosure may be employed virtually anywhere in the vascular system, including within the chambers of the heart, but may prove especially useful in larger vessels, to eliminate the need for large stents or other large fixation mechanisms that could produce adverse effects over time.

Referring again to FIG. 1, system 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation. In some examples, therapy system 10 may include one or more leads or lead segments (not shown in FIG. 1) that deploy one or more electrodes within the systemic circulation (left atrium, left ventricle, artery), accessed trans-septally, or via an epicardial stick. These electrodes may allow alternative electrical sensing configurations that may provide improved or supplemental sensing in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

Programmer 24 shown in FIG. 1 may be a handheld computing device, computer workstation, or networked computing device. Programmer 24 may include electronics and other internal components necessary or desirable for executing the functions associated with the device. In one example, programmer 24 includes one or more processors and memory, as well as a user interface, telemetry module, and power source. In general, memory of programmer 24 may include computer-readable instructions that, when executed by a processor of the programmer, cause it to perform various functions attributed to the device herein. Memory, processor(s), telemetry, and power sources of programmer 24 may include similar types of components and capabilities described above with reference to similar components of IMD 16. Programmer 24 may also be a dedicated wireless system that communicates with IMD 16 remotely, e.g., from the bedside table of patient 14, while the patient sleeps.

In one example, programmer 24 includes a user interface that receives input from a user. The user interface may include, for example, a keypad and a display, which may be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device. For example, a physician may communicate with IMD 16, e.g. program the device by logging into programmer 24 from a remote location via the Internet, a cellular network, or other terrestrial or satellite-based communication network. In one example, programmer 24 may be a fully automated monitoring base station for use in the home of patient 14, with little or no capability for the patient or another user to provide input or programming to IMD 16.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert.

The user may use programmer 24 to program a therapy progression, select electrodes used to deliver electrical stimulation to heart 12 (e.g., in the form of pacing pulses or cardioversion or defibrillation shocks), select waveforms for the electrical stimulation, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication, e.g. via telemetry modules in each of the devices using any number of known techniques. Examples of communication techniques may include, for example, low frequency or RF telemetry, but other techniques are also contemplated. In some examples, programmer 24 may include a programming head that may be placed proximate to the patient's body near the IMD 16 implant site in order to improve the quality or security of communication between IMD 16 and programmer 24.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Other lead configurations may also be used. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing 60 may enclose a signal generator that generates therapeutic stimulation, such as cardiac pacing pulses and defibrillation shocks, as well as a sensing module for monitoring the rhythm of heart 12

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as an intracardiac electrogram (EMG) signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to cause depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

IMD 16 and sensor 38 may be configured to communicate with one another and function in conjunction with one another in a variety of ways. For example, IMD 16 may receive sensor data from sensor 38 and store the data and/or transmit data to programmer 24. Additionally, IMD 16 may analyze data from sensor 38, e.g., for capture detection, tachyarrhythmia detection, or evaluation of cardiac performance parameters, such as contractility, or cardiac output. Cardiac performance parameters may be employed by IMD 16 to adjust therapy parameters, such as CRT parameters, either by a user or automatically in a closed loop configuration.

FIGS. 3A and 3B are elevation and plan views, respectively, of sensor 38 including example fixation device 100 with temporary fixation mechanism 102 and chronic fixation mechanism 103. Sensor 38 also includes battery 104, sensing elements 106, and TCC electrodes 108. In the example of FIGS. 3A and 3B, sensing elements 106 and other electronic components of sensor 38, e.g., a TCC system, is powered by battery 104. Sensing elements 106 may include any suitable sensing elements for sensing a physiological parameter of patient 14, such as, but not limited to capacitive sensing elements to measure internal pressures within patient 14, including, e.g. blood pressure within pulmonary artery 39. In one example, battery 104, sensing elements 106, and other internal components of sensor 38 may be substantially fully encapsulated within an external housing, which, e.g., may be hermetically sealed to inhibit contact of body fluids with the components of the sensor and migration of chemicals within the sensor to the body of patient 14.

Sensor 38 may, in one example, communicate with, e.g., IMD 16 and programmer 24 with a TCC system via TCC electrodes 108 arranged at opposite ends of the sensor. The TCC system of sensor 38 may employ tissue of patient 14 as a communication medium over which information can be sent to and received from IMD 16 and other devices. In another example, sensor 38 may employ, e.g., RF or other telemetry techniques for communicating with IMD 16 and other devices, including, e.g., programmer 24.

Sensor 38 includes fixation device 100 according to this disclosure. Fixation device 100 includes temporary fixation mechanism 102 and chronic fixation mechanism 103, both of which are connected to the housing of sensor 38. Temporary and chronic fixation mechanisms 102, 103, respectively, may be connected to sensor 38 using a variety of techniques. For example, temporary fixation mechanism 102 may be connected to sensor 38 employing the fixation attachment mechanisms described in U.S. application Ser. No. 13/050,417, filed Mar. 17, 2011 and entitled "MEDICAL DEVICE FIXATION ATTACHMENT MECHANISM," the entire content of which is incorporated herein by this reference. Additionally, chronic fixation mechanism 103 may be connected to sensor 38 using adhesives or, in one example, pinching one or more edges of the mechanism in a slot on the outer surface of the sensor. Other appropriate methods for connecting temporary and chronic fixation mechanisms 102, 103, respectively, to sensor 38 are also contemplated for use in examples according to this disclosure.

Temporary fixation mechanism 102 is fabricated from a biodegradable material and is configured to anchor sensor 38 to tissue of patient 14 after implantation until chronic fixation mechanism 103 facilitates sufficient tissue growth to chronically anchor sensor 38, after which the temporary fixation mechanism may be configured to degrade. As noted above, in one example, sensor 38 is implanted in pulmonary artery 39 and configured to sense blood pressure of patient 14, including, e.g., sensing the pressure of blood flowing from the right ventricle outflow tract (RVOT) from right ventricle 28 through the pulmonary valve to pulmonary artery 39 to measure pulmonary artery diastolic pressure (PADP) of patient 14. Example temporary fixation mechanism 102 includes an expandable and contractible structure, such as a stent or stent-like structure, formed from a filament that includes a contoured shape adapted for anchoring sensor 38 within the lumen of a blood vessel or other chamber. In general, such an expandable structure may be expandable in a radial direction, although expansion in other directions is possible. Expandable structures may be self-expanding, or may be expanded by inflation of a balloon, as one example, or other means of applying force to the structure. Where the term stent is used herein, it should be interpreted to generally refer to an expandable and contractible structure that is configured to anchor an IMD to tissue of a patient, e.g. within the lumen of a blood vessel by applying force outward against the lumen walls, or, in other words, against the endothelium of the vessel.

In one example, temporary fixation mechanism 102 includes a biodegradable stent configured to be connected to a first side of sensor 38 as illustrated in FIGS. 3A and 3B. Temporary fixation mechanism 102 is configured to expand into engagement with the endothelium, within the lumen of a blood vessel, e.g. within the lumen of pulmonary artery 39 to push the side of sensor including chronic fixation mechanism 103 against the endothelium of the blood vessel.

In one example, temporary fixation mechanism 102 includes a single filament contoured to form an expandable and contractible stent that anchors sensor 38, or another IMD, within the body of patient 14, e.g. within the lumen of a blood vessel such as pulmonary artery 39. In another example, temporary fixation mechanism 102 may include a number of filaments coupled to form an expandable and contractible stent that anchors sensor 38 within the body of patient 14. Temporary fixation mechanism 102 is fabricated from a biodegradable material such that the fixation mechanism is configured to anchor sensor 38 to tissue of patient 14 after implantation until the temporary fixation mechanism degrades. In one example, temporary fixation mechanism 102 is fabricated from a biodegradable material selected from the group consisting of polyesters, polyurethanes, and combinations thereof. In one example, temporary fixation mechanism 102 is fabricated from a material comprising at least one of polyglycolic acid (PGA), polylactic acid (PLA), polydioxanone (PDS), polyanhydrides, trimethylene carbonate, polyhydroxybutyrate (PHB), polyhydroxyvalerate (PHV), polycaprolactone, polyorthoesters, polyaminoacids, polycyanocrylates, and polyphosphazenes. Additionally, temporary fixation mechanism 102 may be fabricated from a copolymer of any two or more of the foregoing monomers and/or a blend of any two or more polymers listed above and their copolymers. In another example, temporary fixation mechanism 102 is fabricated from one or more biodegradable metals, including, e.g., magnesium (Mg), magnesium alloys, iron (Fe), and iron alloys.

Temporary fixation mechanism 102 and chronic fixation mechanism 103 of fixation device 100 are configured to function in concert to anchor sensor 38 within, e.g., pulmonary artery 39 of patient 14. As such, in one example, temporary fixation mechanism 102 is fabricated from a biodegradable material that is designed to degrade in a period of time that is sufficient to allow enough tissue growth to chronic fixation mechanism 103 to secure sensor 38 in the lumen of pulmonary artery 39. The particular materials and relative amounts of each in the biodegradable material from which temporary fixation mechanism 102 is formed may be varied, in order to vary the duration of time over which the fixation mechanism degrades. Additionally, the absolute amount of material that constitutes temporary fixation mechanism 102 may also be varied to coordinate the degradation of the temporary fixation mechanism with the tissue growth into chronic fixation mechanism 103.

In the example of FIGS. 3A and 3B, chronic fixation mechanism 103 includes a sheet of tissue growth promoting material configured to be connected to the IMD and configured to promote tissue growth into the material to secure the IMD to the tissue of the patient before the temporary fixation mechanism biodegrades. Chronic fixation mechanism 103 is connected to sensor 38 and overlays part of the outer surface of the body of the sensor. As illustrated in FIGS. 3A and 3B, chronic fixation mechanism 103 includes a rectangular sheet of tissue growth promoting material defined by four edges. Two parallel and generally opposing edges of chronic fixation mechanism 103 are attached to the outer surface of sensor 38, e.g. using an adhesive and/or affixing the edges in a slot in the body of the sensor. In one example, chronic fixation mechanism 103 may include a sheet of flexible fabric. In another example, chronic fixation mechanism 103 may include a metallic screen, e.g. a titanium or stainless steel screen. In one example, the tissue growth promoting material from which chronic fixation mechanism 103 is fabricated is selected from the group of materials consisting of tubular-weave polyethylene velour, polyethylene terephthalate (PET), polytetrafluoroethylene (PTFE) mesh, and combinations thereof.

Although example chronic fixation mechanism 103 includes a generally rectangular shape, other examples according to this disclosure may include chronic fixation mechanisms with different shapes, including circular, oval, or irregular shapes. In some such examples, the attachment of the chronic fixation mechanism may differ from that described with reference to example chronic fixation mechanism 103. For example, a circular or oval shaped chronic fixation mechanism may be attached to the outer surface of the body of an IMD, e.g. an implantable sensor along the entire peripheral edge of the mechanism, like along the entire circumference of a circular shaped chronic fixation mechanism.

As noted above, temporary fixation mechanism 102 and chronic fixation mechanism 103 of fixation device 100 are configured to function in concert to anchor sensor 38 within, e.g., pulmonary artery 39 of patient 14. As such, in one example, chronic fixation mechanism 103 is fabricated from a tissue growth promoting material that is designed to facilitate enough tissue in-growth into the chronic fixation mechanism by the time temporary fixation mechanism 102 substantially degrades, thereby chronically securing sensor 38 in the lumen of pulmonary artery 39.

Figure 4:
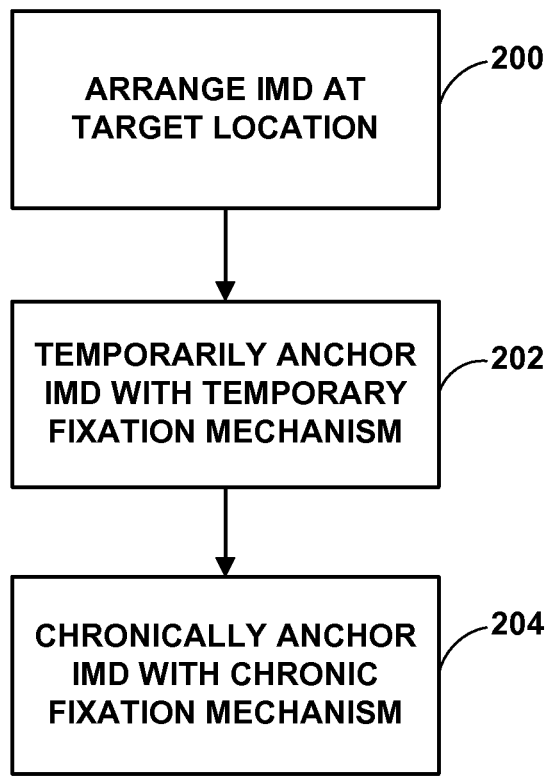
FIG. 4 is a flowchart illustrating an example method of securing an IMD with a fixation device according to this disclosure.

FIG. 4 is a flowchart illustrating an example method of securing an IMD within the body of a patient according to this disclosure. The method of FIG. 4 includes arranging the IMD adjacent to tissue at a target location within the body (200), temporarily anchoring the IMD to the tissue with a temporary fixation mechanism (202), and chronically anchoring the IMD to the tissue with a chronic fixation mechanism (204). The temporary fixation mechanism includes a biodegradable material and is configured to secure the IMD to the tissue after implantation until the temporary fixation mechanism biodegrades. The chronic fixation mechanism is configured to promote sufficient tissue growth such that the mechanism chronically secures the IMD to the tissue before the temporary fixation mechanism biodegrades.

The example method of FIG. 4 is described with reference to sensor 38 and example fixation device 100 of FIGS. 3A and 3B. In particular, the method of FIG. 4 is described with reference to FIGS. 5A-5D, which illustrate the placement of sensor 38 with fixation device 100 in the lumen of pulmonary artery 39 of patient 14. It is noted, however, that the techniques illustrated by the example method of FIG. 4 for securing an IMD within the body of a patient may be applied to other IMDs using different fixation devices in accordance with this disclosure. For example, the techniques of the method of FIG. 4 may be applied to an implantable leadless pacemaker placed in one of the chambers of the heart, e.g. the right ventricle, and secured in the body using a fixation device that includes a temporary fixation mechanism and a chronic fixation mechanism which differ in configuration and/or composition to example temporary fixation mechanism 102 and chronic fixation mechanism 103 of FIGS. 3A, 3B, and 5A-5D.

Figure 5A:
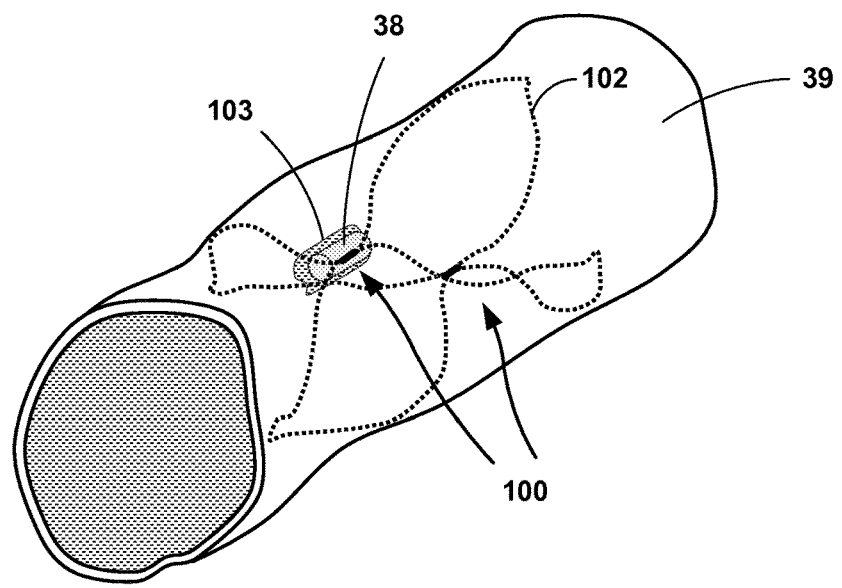
FIGS. 5A-5D are conceptual drawings illustrate the method of FIG. 4 of securing an IMD within a vessel with the fixation device of FIGS. 3A and 3B.
Figure 5B:
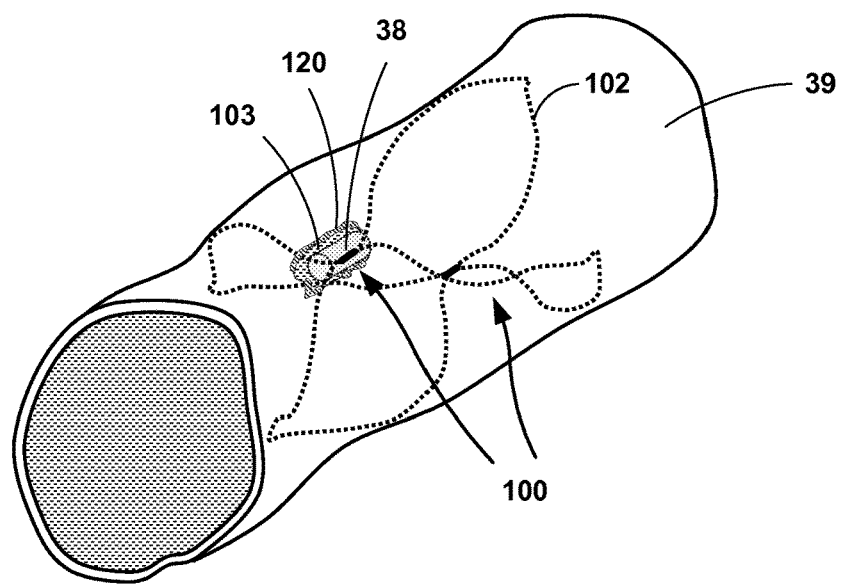
Figure 5C:
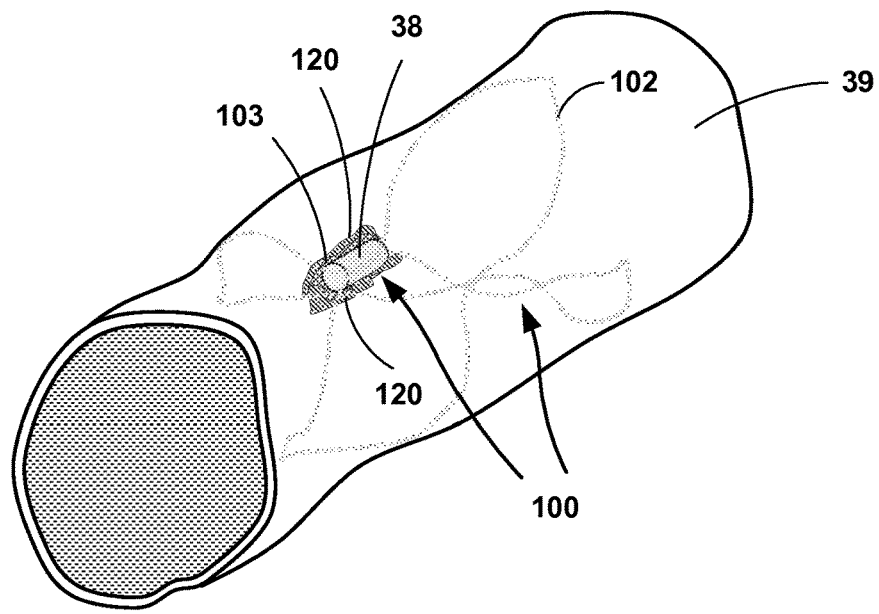
Figure 5D:
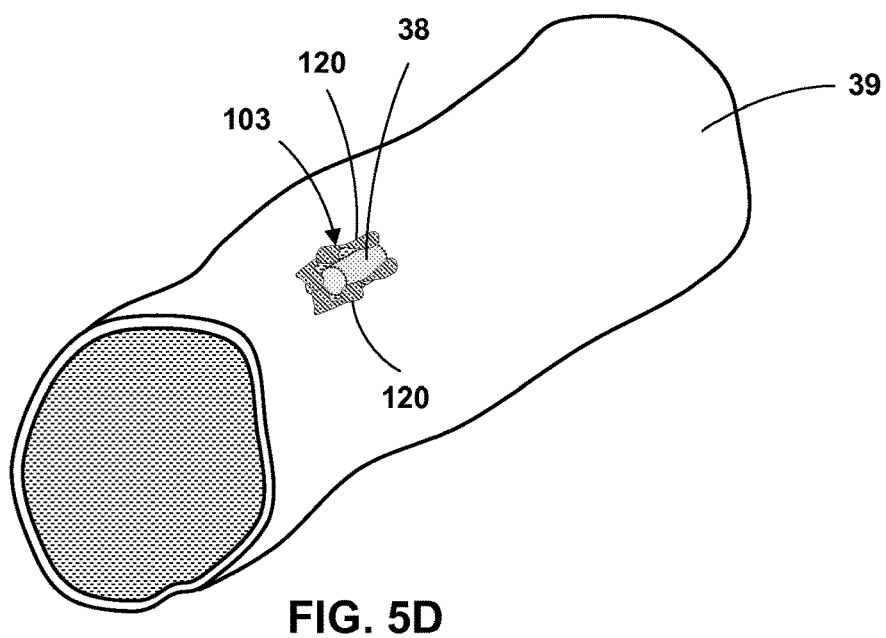

As noted above, FIGS. 5A-5D illustrate the placement of sensor 38 with fixation device 100 in the lumen of pulmonary artery 39 of patient 14. FIG. 5A illustrates the arrangement of sensor 38 in the lumen of pulmonary artery 39 of patient 14 and the temporary anchoring of the sensor with temporary fixation mechanism 102. FIG. 5B illustrates the beginning of tissue growth into the tissue growth promoting sheet of material of which chronic fixation mechanism 103 is comprised. FIG. 5C illustrates the transition between temporary fixation mechanism 102 and chronic fixation mechanism 103 in which the tissue growth into chronic fixation mechanism 103 has advanced sufficiently to hold sensor 38 in place without temporary fixation mechanism 102, and showing such mechanism 102 having begun to degrade. Finally, FIG. 5D illustrates sensor 38 chronically anchored to the endothelium, in the lumen of pulmonary artery 39 of patient 14 with chronic fixation mechanism 103, and temporary fixation mechanism 102 no longer present, i.e. fully degraded.

Referring the example method of FIG. 4 and FIG. 5A, sensor 38 is arranged at a target location within the body of patient 14, which, in the example of FIG. 5A, is a location within the lumen of pulmonary artery 39. Sensor 38, to which fixation device 100 is attached, may be delivered to the target location within the body of patient 14 in a variety of ways. In one example, sensor 38 is delivered to the target location within pulmonary artery 39 using a delivery catheter. The delivery catheter may be employed as part of, e.g., an endoscopic implantation system for guiding sensor 38 to and implanting the sensor at the implantation location within patient 14, e.g. in pulmonary artery 39. In one example, the delivery catheter is directed through a vein into right atrium 26 of patient 14, then right ventricle 28 and through the right ventricle outflow tract (RVOT) from the right ventricle 28 through the pulmonary valve to pulmonary artery 39. The lumen of the delivery catheter may receive sensor 38 and, in one example, a guide wire. The guide wire may be employed to stabilize and guide the placement of sensor 38 at the desired location within the lumen of pulmonary artery 39, and allow the sensor to be accurately placed in more tortuous vasculature. In one example, the catheter may include a guide wire lumen in which the guide wire is arranged. In such an example, the guide wire may be placed at a site distal to the target implant site within patient 14, and sensor 38 may be guided along the guide wire to the site of implant.

Regardless of the particular mode of delivery, once sensor 38 including fixation device 100 is delivered to the target location within the lumen of pulmonary artery 39, the sensor is temporarily anchored in the lumen with temporary fixation mechanism 102 (202). As described above, temporary fixation mechanism 102 may include an expandable and contractible stent. In one example, temporary fixation mechanism 102 is biased into an expanded state. Sensor 38 with fixation device 100 including temporary fixation mechanism 102 attached to the body of the sensor may be delivered to the location within pulmonary artery 39 with temporary fixation mechanism 102 in a contracted state, e.g. held in a contracted state within the lumen of the delivery catheter. When sensor 38 is arranged at the target location, the delivery catheter, or other containment vessel, e.g. a separate sheath, may be refracted to release the biased temporary fixation mechanism 102 such that the stent springs into an expanded state to engage pulmonary artery 39 and to push the side of sensor 38 including chronic fixation mechanism 103 against the endothelium of pulmonary artery 39, as illustrated in FIG. 5A. In this manner, temporary fixation mechanism 102 temporarily anchors sensor 38 within the lumen of pulmonary artery 39, so that chronic fixation mechanism 103 may begin to function to promote tissue growth leading to chronic fixation of sensor 38 to the wall of pulmonary artery 39. Additionally, in this manner, the biasing of temporary fixation mechanism may function to push sensor 38 and chronic fixation mechanism 103 against the endothelium of pulmonary artery 39 (or another vessel in which the sensor 38 is placed) when in an expanded state.

After sensor 38 including fixation device 100 has been arranged at the target location within pulmonary artery 39 and the sensor has been temporarily anchored with temporary fixation mechanism 102, fixation device 100 goes through a transition from temporarily anchoring the sensor within the body of patient 14 to chronically anchoring the sensor with chronic fixation mechanism 103. In one example according to this disclosure, this transition from temporary to chronic fixation of sensor 38 within the body of patient 14 is illustrated in FIGS. 5B and 5C.

Figure 6A:
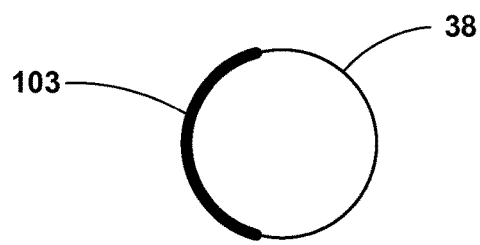
FIGS. 6A-6D are conceptual drawings illustrating a number of different example chronic fixation mechanisms.
Figure 6B:
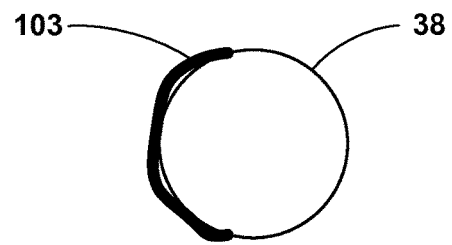

In FIG. 5B, tissue growth 120 into chronic fixation mechanism 103 has begun. However, temporary fixation mechanism 102 remains the primary mechanism by which sensor 38 is anchored to the endothelium, within the lumen of pulmonary artery 39. It should be noted that even if the same or substantially similar sheet of tissue growth promoting material is used for a chronic fixation mechanism according to this disclosure, the configuration of the chronic fixation mechanism with respect to the IMD may affect the function of the fixation mechanism. FIGS. 6A and 6B are schematic illustrations of two different connections between chronic fixation mechanism 103 and an IMD, e.g. sensor 38. As described above, example chronic fixation mechanism 103 includes a rectangular sheet of tissue growth promoting material with two parallel and generally opposing edges attached to the outer surface of sensor 38. In the example of FIG. 6A, the two edges of chronic fixation mechanism 103 are attached to the body of sensor 38 such that the rectangular sheet is pulled taut to lay on the outer surface of the sensor. The arrangement of FIG. 6A may require relatively less material for chronic fixation mechanism 103 and may be less apt to entanglement with other structures during the placement of sensor 38 in pulmonary artery 39. In the example of FIG. 6B, however, the two edges of chronic fixation mechanism 103 are attached to the body of sensor 38 such that the rectangular sheet remains at least partially slack and at least a portion of the rectangular sheet is offset from the outer surface of the sensor. The arrangement of FIG. 6B may facilitate more rapid and/or stronger anchoring of sensor 38 within pulmonary artery 39 because the space between chronic fixation mechanism 103 and the outer surface of the sensor may allow tissue to grow through the sheet of material of which chronic fixation mechanism 103 is comprised and grow between the fixation mechanism and the sensor, thereby potentially more fully incorporating the chronic fixation mechanism and the sensor into the wall of the lumen of pulmonary artery 39.

Figure 6C:
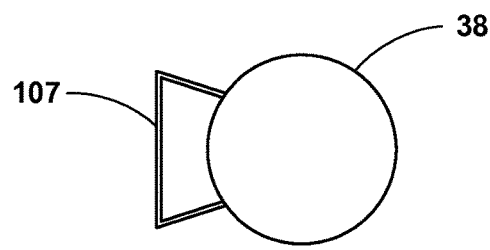

Additionally, as noted above, chronic fixation mechanism 103 may include a sheet of flexible fabric, or, in another example, chronic fixation mechanism 103 may include a metallic screen, e.g. a titanium or stainless steel screen. In examples including a flexible fabric chronic fixation mechanism, such mechanism may not conform to a particular shape, but may, instead, be shaped based on external forces, e.g. gravity and/or tissue or fluids within the body of the patient. Such an example may be illustrated by the configuration of chronic fixation mechanism 103 in FIG. 6B. In examples including a metallic screen chronic fixation mechanism, however, such mechanism may be elastically deformed into different shape configurations, including, e.g. the pedestal shape of chronic fixation mechanism 105 illustrated in FIG. 6C. Example metallic screen chronic fixation mechanism 105 of FIG. 6C may be fabricated from a number of biocompatible metals including, e.g. titanium and stainless steel. Additionally, metallic screen chronic fixation mechanism 105 is, in one example, a sheet of material that forms a pedestal shaped frame. As such, chronic fixation mechanism 105 may be connected to sensor 38 in a manner similar to that described above with reference to chronic fixation mechanism 103. In some examples, metallic screen chronic fixation mechanism 105 may be coated with a material that is configured to promote tissue growth into and around pores in the sheet of screen.

Figure 6D:
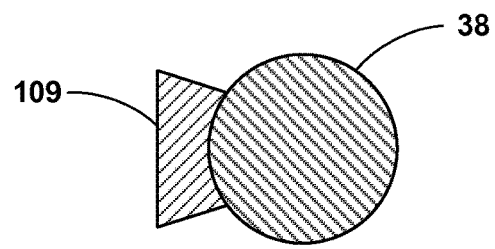

In another example, however, a chronic fixation mechanism according to this disclosure may include a block of material formed into, e.g. a pedestal shape and connected to an IMD. For example, FIG. 6D is a cross-sectional view of sensor 38 with chronic fixation mechanism 109 connected to one side of sensor 38. In this example, instead of being formed from a sheet of material that forms a frame in a pedestal shape, chronic fixation mechanism 109 is formed from a block of material that forms a substantially solid pedestal connected to sensor 38. In such examples, chronic fixation mechanism 109 may be formed with surface features, e.g. surface variations and/or pores, or may be coated with a material configured to promote tissue growth to chronically anchor sensor 38 to tissue within a patient, or even may have attached, in some manner, a flexible, growth-promoting fabric, similar to that discussed in regard to FIGS. 6A-6B.

Referring again to the method of FIG. 4 and FIGS. 5A-5D, FIG. 5C illustrates the transition between temporary and chronic fixation of sensor 38 within pulmonary artery 39 in which tissue growth 120 into chronic fixation mechanism 103 has advanced and temporary fixation mechanism 102 has begun to degrade. And, finally, in FIG. 5D, sensor 38 is chronically anchored within pulmonary artery 39 by chronic fixation mechanism 103 (204) via tissue growth 120 having advanced further into the chronic fixation mechanism to secure the sensor to the wall of the lumen of pulmonary artery 39, at which point temporary fixation mechanism 102 may have substantially degraded. The time period over which the transition between temporary and chronic fixation of sensor 38 within the body of patient 14 illustrated in FIGS. 5B and 5C occurs may be days, weeks, or months, e.g., depending on the safety profile applicable for a given device and/or implant site. However, as noted above, temporary fixation mechanism 102 and chronic fixation mechanism 103 are configured to function in concert such that enough tissue growth 120 into chronic fixation mechanism 103 occurs before or, at the least, by the time temporary fixation mechanism 102 substantially degrades.

Figure 7:
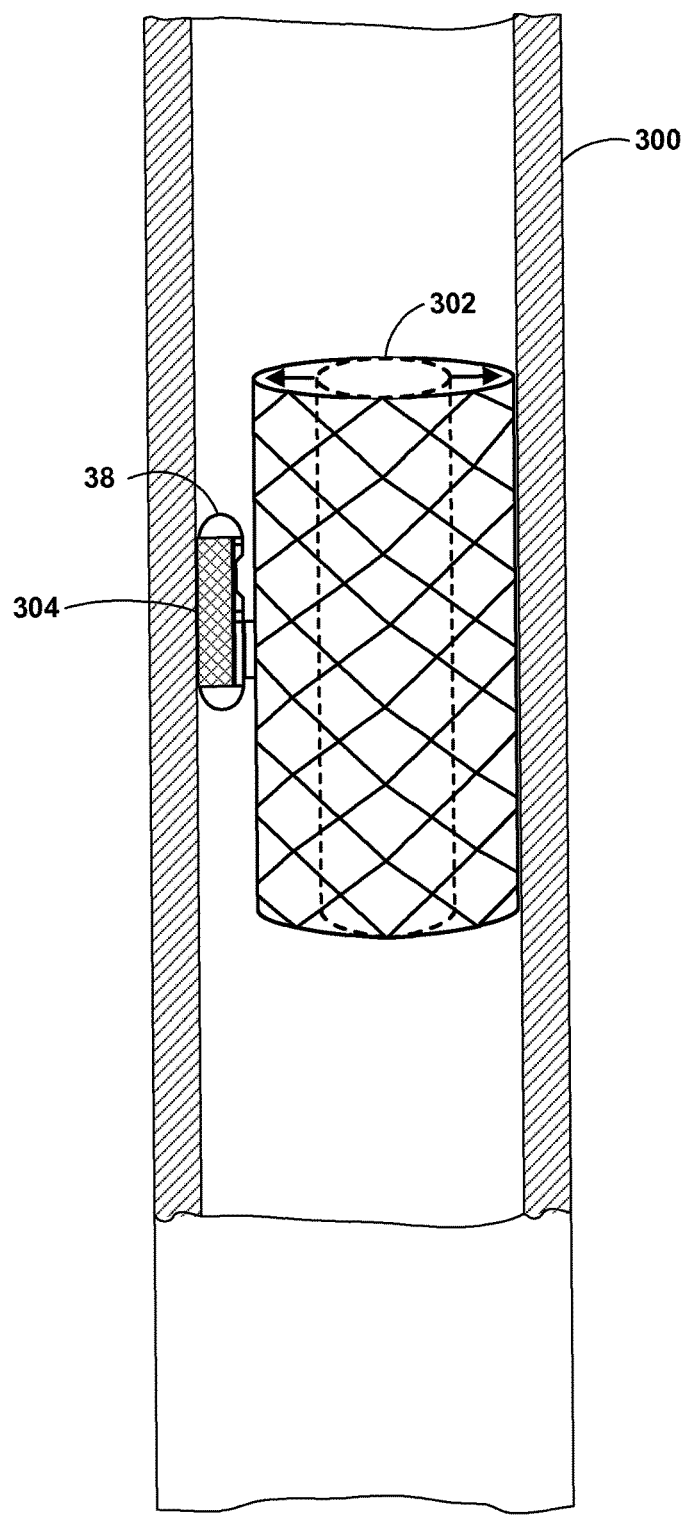
FIG. 7 is a conceptual drawing illustrating an implantable sensor temporarily anchored with an example temporary fixation mechanism.
Figure 9A:
FIGS. 9A-9J are conceptual drawings illustrating a number of example temporary fixation mechanisms that may be employed in examples according to this disclosure.
Figure 9B:
Figure 9C:
Figure 9D:
Figure 9E:
Figure 9F:
Figure 9G:
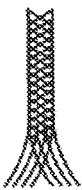
Figure 9H:
Figure 9I:
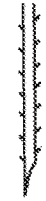
Figure 9J:
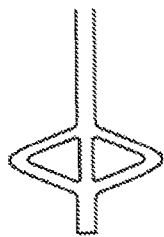

Although the foregoing examples have been described with reference to example temporary fixation mechanism 102 including the expandable and contractible stent illustrated in FIGS. 3A, 3B, and 5A-5D, in other examples a temporary fixation mechanism according to this disclosure may include a number of different configurations. For example, FIG. 7 illustrates sensor 38 anchored within blood vessel 300 with an example fixation device including expandable temporary fixation mechanism 302 and chronic fixation mechanism 304. In one example, chronic fixation mechanism 304 may be substantially similar to chronic fixation mechanism 103 described above. Additionally, chronic fixation mechanism 304 may be connected to sensor 38 in the manner described with reference to either FIG. 6A or 6B such that the sheet of tissue growth promoting material is either pulled taut to lay against or is slack such that part of the sheet is offset from the outer surface of the sensor, or in a manner like that of FIG. 6C or 6D, with a pedestal and any number of means of chronic fixation, metal screen coated or uncoated, or solid material, coated or uncoated, or either screen or solid material with fabric, or any combination of the above that maximizes tissue ingrowth and chronic attachment integrity.

Temporary fixation mechanism 302 includes a cylindrical, expandable and contractible stent that is configured to temporarily anchor sensor 38 within vessel 300. The biodegradable materials and properties of temporary fixation mechanism 302 may be substantially similar to those of temporary fixation mechanism 102 described above. In the example of FIG. 7, temporary fixation mechanism 302 includes a mesh stent with a plurality of material segments each of which is pivotally joined at either end to another segment at a vertex. The material segments of which temporary fixation mechanism 302 is comprised may be constructed from various biodegradable materials that are configured to temporarily anchor sensor 38 within blood vessel 300 and degrade over time until chronic fixation mechanism 304 chronically anchors the sensor within the vessel. In one example, temporary fixation mechanism 302 is expandable and contractible by rotation of the material segments with respect to each other at the plurality of vertices at which the segments are pivotally joined. As temporary fixation mechanism 302 contracts, the material segments rotate such that the angle of each segment with respect to a longitudinal axis of the temporary fixation mechanism decreases, which in turn decreases the diameter and increases the overall length of the lead member. Conversely, as temporary fixation mechanism 302 expands, the material segments rotate such that the angle of each segment with respect to the longitudinal axis of the temporary fixation mechanism increases, which in turn increases the diameter and decreases the overall length of the lead member. In another example, sensor 38 may be mounted to fixation mechanism 302 in a similar manner to that of FIG. 7, except that it is mounted on the inside of fixation mechanism 302, rather than the outside. Either of these approaches may work well, depending on other conditions, but the intent of both is to hold chronic fixation mechanism 304 against the endothelium of vessel 300.

FIG. 8 is a plan view of sensor 38 including example fixation device 400 with temporary fixation mechanism 402 and chronic fixation mechanism 403. Sensor 38 also includes battery 104, sensing elements 106, and TCC electrodes 108. In the example of FIGS. 3A and 3B, sensing elements 106 and other electronic components of sensor 38, e.g., a TCC system, is powered by battery 104. Sensor 38, components thereof and fixation device 400 may be configured and function in substantially similar manner as described with reference to the example of FIGS. 3A and 3B, and 5A-5D. However, temporary fixation mechanism 402 is connected to sensor 38 such that sensor 38 is arranged within temporary fixation mechanism 402. In this example, part of temporary fixation mechanism 402 is connected to the same side of sensor 38 to which chronic fixation mechanism 403 is connected. In this example and similar arrangements of an IMD and fixation devices according to this disclosure, tissue growth promoted by chronic fixation mechanism 403 may occur around temporary fixation mechanism 402, which may thereafter biodegrade to leave sensor 38 anchored to tissue of a patient by chronic fixation mechanism 403.

In some examples according to this disclosure, a temporary fixation mechanism may include a mechanism for securing an IMD that differs from an expandable and contractible stent, such as those described with reference to temporary fixation mechanisms 102 of FIGS. 3A and 3B, 302 of FIG. 7, and 402 of FIG. 8. A temporary fixation mechanism according to this disclosure may include a mechanism that is configured to secure an IMD at a target location by penetrating or pinching tissue adjacent the location. For example, a temporary fixation mechanism according to this disclosure may include one or a combination of barbs, tines, hooks, harpoons, or threaded, helical, or other anchors that are configured to penetrate or pinch tissue to secure an IMD within the body of a patient. As with the example stents described above, such temporary fixation mechanisms are fabricated from a biodegradable material and are configured to anchor the IMD to the tissue of the patient after implantation until the temporary fixation mechanism biodegrades in accordance with the examples described above. Examples of a number of types of anchors which may be employed as temporary fixation mechanisms in examples according to this disclosure are illustrated in FIGS. 9A-9J.

Although fixation techniques according to this disclosure are described in the context of cardiac devices, and, in particular, sensors for cardiac systems, the examples disclosed herein may also be employed to place other types of implantable medical devices. In some examples, a fixation device including temporary and chronic fixation mechanisms in accordance with this disclosure may be employed with medical devices that deliver therapy via a medical lead. For example, a fixation device in accordance with the disclosed examples may be employed in a neurostimulation system for spinal cord, gastric, pelvic floor, or deep brain stimulation delivered via one or more electrical stimulation leads. In another example, the examples disclosed herein may be used in conjunction with implantable fluid delivery systems, e.g., implantable drug pumps that are configured to deliver therapeutic fluids via a catheter. A fixation device in accordance with this disclosure may also be employed with an implantable microstimulator. For example, a fixation device in accordance with this disclosure may be employed with an implantable leadless pacemaker configured to be implanted, e.g., within the right ventricle of a patient's heart to deliver one or more of pacing, cardioversion, and/or defibrillation to the patient.

In addition, systems according to this disclosure are not limited to treatment of a human patient. In alternative examples, therapy system 10 may be implemented in non-human patients, e.g., primates, canines, equines, pigs, and felines. These other animals may undergo clinical or research therapies that may benefit from the subject matter of this disclosure.

Some techniques described in this disclosure, including those attributed to IMD 16, programmer 24, sensor 38, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" as used herein may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure. The term "memory" as used herein may generally refer to any of the foregoing types of computer-readable storage media, alone or in combination with other logic circuitry, or any other equivalent circuitry. The computer-readable storage medium may be nontransitory.

Various examples have been described. These and other examples are within the scope of the following claims.

The invention claimed is:
1. An implantable medical device (IMD) comprising:
a body containing electronics;
a fixation device connected to the body of the device, wherein the fixation device comprises:
a temporary fixation mechanism comprising a biodegradable material and configured to anchor the IMD within a blood vessel of a patient after implantation until the temporary fixation mechanism biodegrades; and a chronic fixation mechanism overlaying a first side of the body and configured to promote tissue growth along the first side of the body that anchors the IMD within the blood vessel of the patient before the temporary fixation mechanism biodegrades such that the chronic fixation mechanism is configured to more permanently anchor the IMD to the blood vessel than the temporary fixation mechanism, wherein the temporary fixation mechanism is configured to anchor the IMD within the blood vessel such that the first side of the body including the chronic fixation mechanism is arranged against endothelium of the blood vessel, and wherein the chronic fixation mechanism comprises a sheet of tissue growth promoting material configured to be connected to the IMD housing and configured to promote tissue growth into the material to secure the IMD within the blood vessel of the patient before the temporary fixation mechanism biodegrades, wherein the sheet of tissue growth promoting material comprises a rectangular sheet of tissue growth promoting material defined by four edges, and wherein a first edge is attached to the outer surface of the IMD housing and a second edge generally parallel to and offset from the first edge is attached to the outer surface of the IMD housing.

2. The IMD of claim 1, wherein the temporary fixation mechanism comprises a biodegradable stent configured to be connected to at least one of a first side or a second side of the body of the IMD generally opposite the first side such that the stent is configured to push the first side of the body of the IMD including the chronic fixation mechanism against the endothelium of the blood vessel.

3. The IMD of claim 1, wherein the blood vessel of the patient comprises at least one of the right or the left first branches of the pulmonary artery, a systemic vessel, a brain vessel, or a renal vessel.

4. The IMD of claim 1, wherein the temporary fixation mechanism comprises at least one of polyglycolic acid (PGA), poly lactic acid (PLA), polydioxanone (PDS), polyanhydrides, trimethylene carbonate, polyhydroxybutyrate (PHB), polyhydroxyvalerate (PHV), polycaprolactone, polyorthoesters, polyaminoacids, polycyanocrylates, and polyphosphazenes.

5. The IMD of claim 1, wherein the temporary fixation mechanism comprises a biodegradable material selected from the group consisting of polyesters, polyurethanes, and combinations thereof.

6. The IMD of claim 1, wherein the temporary fixation mechanism comprises a biodegradable material selected from the group consisting of polyglycolic acid (PGA), polylactic acid (PLA), and combinations thereof.

7. The IMD of claim 1, wherein the temporary fixation mechanism comprises a biodegradable material selected from the group consisting of magnesium, magnesium alloys, iron, iron alloys, and combinations thereof.

8. The IMD of claim 1, wherein the temporary fixation mechanism comprises a biodegradable material configured to substantially degrade by a first time sufficient to allow enough tissue growth to the chronic fixation mechanism to secure the IMD within the blood vessel of the patient.

9. The IMD of claim 1, wherein the sheet of tissue growth promoting material is configured overlay at least part of an outer surface of the body.

10. The IMD of claim 1, wherein the sheet of tissue growth promoting material comprises a sheet of flexible fabric.

11. The IMD of claim 1, wherein the first and second edges of the rectangular sheet of tissue growth promoting material are attached to the body of the IMD such that the rectangular sheet of tissue growth promoting material is pulled taut to lay on the outer surface of the body of the IMD.

12. The IMD of claim 1, wherein the first and second edges of the rectangular sheet of tissue growth promoting material are attached to the body of the IMD such that the rectangular sheet of tissue growth promoting material remains at least partially slack and at least a portion of the rectangular sheet of tissue growth promoting material is offset from the outer surface of the body of the IMD.

13. The IMD of claim 1, wherein the sheet of tissue growth promoting material is selected from the group consisting of tubular-weave polyethylene velour, polyethylene terephthalate (PET), polytetrafluoroethylene (PTFE) mesh, and combinations thereof.

14. The IMD of claim 1, wherein the sheet of tissue growth promoting material comprises a sheet of metallic screen.

15. The IMD of claim 14, wherein the sheet of metallic screen comprises at least one of titanium and stainless steel.

16. The IMD of claim 1, wherein the electronics include a least one of a battery, a telemetry module, sensing elements and a signal generator configured to generate electrical stimulation.

17. An assembly comprising:

an implantable medical device (IMD) comprising a housing containing electronics; and a fixation device for the IMD, the fixation device comprising:

a temporary fixation mechanism connected to the IMD, wherein the temporary fixation mechanism comprises a biodegradable material and is configured to anchor the IMD within a blood vessel of a patient after implantation until the temporary fixation mechanism biodegrades; and a chronic fixation mechanism overlaying a first side of the IMD housing, wherein the chronic fixation mechanism is configured to promote tissue growth along the first side of the IMD housing that anchors the IMD within the blood vessel before the temporary fixation mechanism biodegrades such that the chronic fixation mechanism is configured to more permanently anchor the IMD to the blood vessel than the temporary fixation mechanism, wherein the chronic fixation mechanism comprises a sheet of tissue growth promoting material configured to be connected to the IMD housing and configured to promote tissue growth into the material to secure the IMD within the blood vessel of the patient before the temporary fixation mechanism biodegrades, wherein the sheet of tissue growth promoting material comprises a rectangular sheet of tissue growth promoting material defined by four edges, and wherein a first edge is attached to the outer surface of the IMD housing and a second edge generally parallel to and offset from the first edge is attached to the outer surface of the IMD housing, and wherein the temporary fixation mechanism is configured to anchor the IMD within the blood vessel such that the first side of the IMD housing, including the chronic fixation mechanism, is arranged against endothelium of the blood vessel.

18. The assembly of claim 17, wherein the temporary fixation mechanism comprises a biodegradable stent configured to be connected to at least one of the first side or a second side of the IMD housing such that the stent is configured to push the first side of the IMD housing, including the chronic fixation mechanism, against the endothelium of the blood vessel.

19. The assembly of claim 17, wherein the blood vessel of the patient comprises at least one of the right or the left branches of the pulmonary artery, a systemic vessel, a brain vessel, or a renal vessel.

20. The assembly of claim 17, wherein the temporary fixation mechanism comprises at least one of polyglycolic acid (PGA), polylactic acid (PLA), polydioxanone (PDS), polyanhydrides, trimethylene carbonate, polyhydroxybutyrate (PHB), polyhydroxyvalerate (PHV), polycaprolactone, polyorthoesters, polyaminoacids, polycyanocrylates, and polyphosphazenes.

21. The assembly of claim 17, wherein the temporary fixation mechanism comprises a biodegradable material selected from the group consisting of polyesters, polyurethanes, and combinations thereof.

22. The assembly of claim 17, wherein the temporary fixation mechanism comprises a biodegradable material selected from the group consisting of polyglycolic acid (PGA), polylactic acid (PLA), and combinations thereof.

23. The assembly of claim 17, wherein the temporary fixation mechanism comprises a biodegradable material selected from the group consisting of magnesium, magnesium alloys, iron, iron alloys, and combinations thereof.

24. The assembly of claim 17, wherein the temporary fixation mechanism comprises a biodegradable material configured to substantially degrade by a first time sufficient to allow enough tissue growth to the chronic fixation mechanism to secure the IMD within the blood vessel of the patient.

25. The assembly of claim 17, wherein the sheet of tissue growth promoting material is configured to at least part of an outer surface of the IMD housing.

26. The assembly of claim 17, wherein the sheet of tissue growth promoting material comprises a sheet of flexible fabric.

27. The assembly of claim 17, wherein the first and second edges of the rectangular sheet of tissue growth promoting material are attached to the IMD housing such that the rectangular sheet of tissue growth promoting material is pulled taut to lay on the outer surface of the IMD housing.

28. The assembly of claim 17, wherein the first and second edges of the rectangular sheet of tissue growth promoting material are attached to the IMD housing such that the rectangular sheet of tissue growth promoting material remains at least partially slack and at least a portion of the rectangular sheet is offset from the outer surface of the IMD housing.

29. The assembly of claim 17, wherein the sheet of tissue growth promoting material is selected from the group consisting of tubular-weave polyethylene velour, polyethylene terephthalate (PET), polytetrafluoroethylene (PTFE) mesh, and combinations thereof.

30. The assembly of claim 17, wherein the sheet of tissue growth promoting material comprises a sheet of metallic screen.

31. The assembly of claim 30, wherein the sheet of metallic screen comprises at least one of titanium and stainless steel.

32. The assembly of claim 30, wherein the sheet of metallic screen forms a pedestal protruding from the first side of the housing such that the housing of the IMD is offset from the endothelium of the blood vessel.

33. The assembly of claim 17, wherein the electronics include a least one of a battery, a telemetry module, sensing elements and a signal generator configured to generate electrical stimulation.

34. A method of securing an implantable medical device (IMD) within the body of a patient, the method comprising:
arranging the IMD at a target location within a blood vessel of the patient, wherein the IMD comprises a housing containing electronics;
temporarily anchoring the IMD within the blood vessel with a temporary fixation mechanism comprising a biodegradable material, wherein the temporary fixation mechanism is configured to secure the IMD within the blood vessel after implantation until the temporary fixation mechanism biodegrades; and
chronically anchoring the IMD within the blood vessel with a chronic fixation mechanism overlaying a first side of the IMD housing and configured to promote tissue growth along the first side of the IMD housing that secures the IMD within the blood vessel before the temporary fixation mechanism biodegrades, wherein the chronic fixation mechanism is configured to more permanently anchor the IMD to the blood vessel than the temporary fixation mechanism,
wherein the temporary fixation mechanism is configured to anchor the IMD within the blood vessel such that the first side of the IMD housing including the chronic fixation mechanism is arranged against endothelium of the blood vessel, and
wherein the chronic fixation mechanism comprises a sheet of tissue growth promoting material configured to be connected to the IMD housing and configured to promote tissue growth into the material to secure the IMD within the blood vessel of the patient before the temporary fixation mechanism biodegrades, wherein the sheet of tissue growth promoting material comprises a rectangular sheet of tissue growth promoting material defined by four edges, and wherein a first edge is attached to the outer surface of the IMD housing and a second edge generally parallel to and offset from the first edge is attached to the outer surface of the IMD housing.

35. The method of claim 34, wherein the electronics include a least one of a battery, a telemetry module, sensing elements and a signal generator configured to generate electrical stimulation.

* * * * *